(12) United States Patent
Moore et al.

(10) Patent No.: US 6,569,419 B2
(45) Date of Patent: May 27, 2003

(54) METHODS FOR PROMOTING PRODUCTION OF MYELIN BY SCHWANN CELLS

(75) Inventors: Emma E. Moore, Seattle, WA (US); Julia E. Novak, Bainbridge Island, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/794,705

(22) Filed: Feb. 27, 2001

(65) Prior Publication Data

US 2002/0039568 A1 Apr. 4, 2002

Related U.S. Application Data

(60) Provisional application No. 60/185,666, filed on Feb. 29, 2000.

(51) Int. Cl.[7] ............................................... A61K 38/19

(52) U.S. Cl. ............................... 424/85.1; 514/2; 514/8; 514/12

(58) Field of Search ................... 514/2, 8, 12; 424/85.1

(56) References Cited

FOREIGN PATENT DOCUMENTS

| WO | WO98/49310 | 11/1998 |
|---|---|---|

*Primary Examiner*—Prema Mertz
(74) *Attorney, Agent, or Firm*—Paul G. Lunn, Esq.

(57) ABSTRACT

A method for promoting the expression of myelin or Protein Zero in Schwann cells using Zcyto7 or IL-17. Zcyto7 or IL-17 are further used to promote myelination of the peripheral nervous system. This is particularly useful in treating diseases dymyelinating diseases such as diabetic neuropathy, Guillain-Barré Syndrome, chronic demyelinating disease, acute demyelinating polyneuropathy and human immunodeficiency viral demyelinating neuropathy or demyelination caused by trauma.

1 Claim, No Drawings

SEQUENCE LISTING

<160> NUMBER OF SEQ ID NOS: 28

<210> SEQ ID NO 1
<211> LENGTH: 736
<212> TYPE: DNA
<213> ORGANISM: Homo sapiens
<220> FEATURE:
<221> NAME/KEY: CDS
<222> LOCATION: (57)...(596)

<400> SEQUENCE: 1

```
gaattcggca cgaggaggcg ggcagcagct gcaggctgac cttgcagctt ggcgga atg      59
                                                              Met
                                                                1 gac tgg cct cac aac ctg ctg ttt ctt ctt acc att tcc atc ttc ctg       107
Asp Trp Pro His Asn Leu Leu Phe Leu Leu Thr Ile Ser Ile Phe Leu
        5                   10                  15 ggg ctg ggc cag ccc agg agc ccc aaa agc aag agg aag ggg caa ggg       155
Gly Leu Gly Gln Pro Arg Ser Pro Lys Ser Lys Arg Lys Gly Gln Gly
 20                  25                  30 cgg cct ggg ccc ctg gcc cct ggc cct cac cag gtg cca ctg gac ctg       203
Arg Pro Gly Pro Leu Ala Pro Gly Pro His Gln Val Pro Leu Asp Leu
 35                  40                  45 gtg tca cgg atg aaa ccg tat gcc cgc atg gag gag tat gag agg aac       251
Val Ser Arg Met Lys Pro Tyr Ala Arg Met Glu Glu Tyr Glu Arg Asn
 50                  55                  60                  65 atc gag gag atg gtg gcc cag ctg agg aac agc tca gag ctg gcc cag       299
Ile Glu Glu Met Val Ala Gln Leu Arg Asn Ser Ser Glu Leu Ala Gln
                 70                  75                  80 aga aag tgt gag gtc aac ttg cag ctg tgg atg tcc aac aag agg agc       347
Arg Lys Cys Glu Val Asn Leu Gln Leu Trp Met Ser Asn Lys Arg Ser
             85                  90                  95 ctg tct ccc tgg ggc tac agc atc aac cac gac ccc agc cgt atc ccc       395
Leu Ser Pro Trp Gly Tyr Ser Ile Asn His Asp Pro Ser Arg Ile Pro
            100                 105                 110 gtg gac ctg ccg gag gca cgg tgc ctg tgt ctg ggc tgt gtg aac ccc       443
Val Asp Leu Pro Glu Ala Arg Cys Leu Cys Leu Gly Cys Val Asn Pro
    115                 120                 125 ttc acc atg cag gag gac cgc agc atg gtg agc gtg ccg gtg ttc agc       491
Phe Thr Met Gln Glu Asp Arg Ser Met Val Ser Val Pro Val Phe Ser
130                 135                 140                 145 cag gtt cct gtg cgc cgc cgc ctc tgc ccg cca ccg ccc cgc aca ggg       539
Gln Val Pro Val Arg Arg Arg Leu Cys Pro Pro Pro Pro Arg Thr Gly
                150                 155                 160 cct tgc cgc cag cgc gca gtc atg gag acc atc gct gtg ggc tgc acc       587
Pro Cys Arg Gln Arg Ala Val Met Glu Thr Ile Ala Val Gly Cys Thr
                165                 170                 175 tgc atc ttc tgaatcacct ggcccagaag ccaggccagc agcccgagac              636
Cys Ile Phe
        180 catcctcctt gcacctttgt gccaagaaag gcctatgaaa agtaaacact gactttgaa      696 agccagaaaa aaaaaaaaaa aaaaaaattc ctgcggccgc                           736
```

<210> SEQ ID NO 2
<211> LENGTH: 180
<212> TYPE: PRT
<213> ORGANISM: Homo sapiens

<400> SEQUENCE: 2

```
Met Asp Trp Pro His Asn Leu Leu Phe Leu Leu Thr Ile Ser Ile Phe
 1               5                  10                  15

Leu Gly Leu Gly Gln Pro Arg Ser Pro Lys Ser Lys Arg Lys Gly Gln
            20                  25                  30

Gly Arg Pro Gly Pro Leu Ala Pro Gly Pro His Gln Val Pro Leu Asp
            35                  40                  45

Leu Val Ser Arg Met Lys Pro Tyr Ala Arg Met Glu Glu Tyr Glu Arg
    50                  55                  60

Asn Ile Glu Glu Met Val Ala Gln Leu Arg Asn Ser Ser Glu Leu Ala
65                  70                  75                  80

Gln Arg Lys Cys Glu Val Asn Leu Gln Leu Trp Met Ser Asn Lys Arg
                85                  90                  95

Ser Leu Ser Pro Trp Gly Tyr Ser Ile Asn His Asp Pro Ser Arg Ile
                100                 105                 110

Pro Val Asp Leu Pro Glu Ala Arg Cys Leu Cys Leu Gly Cys Val Asn
            115                 120                 125

Pro Phe Thr Met Gln Glu Asp Arg Ser Met Val Ser Val Pro Val Phe
            130                 135                 140

Ser Gln Val Pro Val Arg Arg Leu Cys Pro Pro Pro Arg Thr
145                 150                 155                 160

Gly Pro Cys Arg Gln Arg Ala Val Met Glu Thr Ile Ala Val Gly Cys
                165                 170                 175

Thr Cys Ile Phe
            180

<210> SEQ ID NO 3
<211> LENGTH: 397
<212> TYPE: DNA
<213> ORGANISM: Homo sapiens
<220> FEATURE:
<221> NAME/KEY: variation
<222> LOCATION: (0)...(0)
<223> OTHER INFORMATION: 'n' in the sequence is any nucleotide

<400> SEQUENCE: 3
aggcgggcan agctgcaggc tgaccttgca gcttggcgga atggactggc ctcacaacct      60
gctgtttctt cttaccattt ccatcttcct ggggctgggc agccaggagc cccaaaagca    120
agaggaaggg gcaagggcgg cctgggcccn tggcctggcc tcaccaggtg ccactggacc    180
tggtgtcacg gatgaaaccg tatgcccgca tggaggagta tgagaggaac atcgaggaga    240
tggtggccca gctgaggaac agctcanaag ctggcccaga gaaagtgtga ggtcaacttg    300
cagctgtgga tgtccaacaa gaaggagcct gtctcccttg gggctacaag catcaaccac    360
cgacccaagc cgtatccccg tgggaccttg ccgggac                             397

<210> SEQ ID NO 4
<211> LENGTH: 18
<212> TYPE: DNA
<213> ORGANISM: Homo sapiens

<400> SEQUENCE: 4
ttaccatttc catcttcc                                                    18

<210> SEQ ID NO 5
<211> LENGTH: 18
<212> TYPE: DNA
<213> ORGANISM: Homo sapiens

<400> SEQUENCE: 5
```

```
ccettcctct tgcttttg                                                  18

<210> SEQ ID NO 6
<211> LENGTH: 692
<212> TYPE: DNA
<213> ORGANISM: Homo sapiens
<220> FEATURE:
<221> NAME/KEY: CDS
<222> LOCATION: (50)...(589)

<400> SEQUENCE: 6 gggttcctg gcgggtggca gctgcgggcc tgccgcctga cttggtggg atg gac tgg     58
                                                     Met Asp Trp
                                                      1 ccg cac agc ctg ctc ttc ctc ctg gcc atc tcc atc ttc ctg gcg cca    106
Pro His Ser Leu Leu Phe Leu Leu Ala Ile Ser Ile Phe Leu Ala Pro
  5                  10                  15 agc cac ccc cgg aac acc aaa ggc aaa aga aaa ggg caa ggg agg ccc    154
Ser His Pro Arg Asn Thr Lys Gly Lys Arg Lys Gly Gln Gly Arg Pro
 20                  25                  30                  35 agt ccc ttg gcc cct ggg cct cat cag gtg ccg ctg gac ctg gtg tct    202
Ser Pro Leu Ala Pro Gly Pro His Gln Val Pro Leu Asp Leu Val Ser
                 40                  45                  50 cga gta aag ccc tac gct cga atg gaa gag tat gag cgg aac ctt ggg    250
Arg Val Lys Pro Tyr Ala Arg Met Glu Glu Tyr Glu Arg Asn Leu Gly
             55                  60                  65 gag atg gtg gcc cag ctg agg aac agc tcc gag cca gcc aag aag aaa    298
Glu Met Val Ala Gln Leu Arg Asn Ser Ser Glu Pro Ala Lys Lys Lys
         70                  75                  80 tgt gaa gtc aat cta cag ctg tgg ttg tcc aac aag agg agc ctg tcc    346
Cys Glu Val Asn Leu Gln Leu Trp Leu Ser Asn Lys Arg Ser Leu Ser
     85                  90                  95 cca tgg ggc tac agc atc aac cac gac ccc agc cgc atc cct gcg gac    394
Pro Trp Gly Tyr Ser Ile Asn His Asp Pro Ser Arg Ile Pro Ala Asp
100                 105                 110                 115 ttg ccc gag gcg cgg tgc cta tgt ttg ggt tgc gtg aat ccc ttc acc    442
Leu Pro Glu Ala Arg Cys Leu Cys Leu Gly Cys Val Asn Pro Phe Thr
                120                 125                 130 atg cag gag gac cgt agc atg gtg agc gtg cca gtg ttc agc cag gtg    490
Met Gln Glu Asp Arg Ser Met Val Ser Val Pro Val Phe Ser Gln Val
            135                 140                 145 ccg gtg cgc cgc cgc ctc tgt cct caa cct cct cgc cct ggg ccc tgc    538
Pro Val Arg Arg Arg Leu Cys Pro Gln Pro Pro Arg Pro Gly Pro Cys
        150                 155                 160 cgc cag cgt gtc gtc atg gag acc atc gct gtg ggt tgc acc tgc atc    586
Arg Gln Arg Val Val Met Glu Thr Ile Ala Val Gly Cys Thr Cys Ile
    165                 170                 175 ttc tgagccaacc accaacccgg tggcctctgc aacaaccctc cctccctgca          639
cccactgtga ccctcaaggc tgataaacag taaacgctgt tctttgtaaa gga          692

<210> SEQ ID NO 7
<211> LENGTH: 179
<212> TYPE: PRT
<213> ORGANISM: Homo sapiens

<400> SEQUENCE: 7

Met Asp Trp Pro His Ser Leu Leu Phe Leu Leu Ala Ile Ser Ile Phe
  1               5                  10                  15

Leu Ala Pro Ser His Pro Arg Asn Thr Lys Gly Lys Arg Lys Gly Gln
             20                  25                  30
```

-continued

Gly Arg Pro Ser Pro Leu Ala Pro Gly Pro His Gln Val Pro Leu Asp
         35                  40                  45

Leu Val Ser Arg Val Lys Pro Tyr Ala Arg Met Glu Glu Tyr Glu Arg
 50                  55                  60

Asn Leu Gly Glu Met Val Ala Gln Leu Arg Asn Ser Ser Glu Pro Ala
 65                  70                  75                  80

Lys Lys Lys Cys Glu Val Asn Leu Gln Leu Trp Leu Ser Asn Lys Arg
             85                  90                  95

Ser Leu Ser Pro Trp Gly Tyr Ser Ile Asn His Asp Pro Ser Arg Ile
            100                 105                 110

Pro Ala Asp Leu Pro Glu Ala Arg Cys Leu Cys Leu Gly Cys Val Asn
            115                 120                 125

Pro Phe Thr Met Gln Glu Asp Arg Ser Met Val Ser Val Pro Val Phe
        130                 135                 140

Ser Gln Val Pro Val Arg Arg Arg Leu Cys Pro Gln Pro Pro Arg Pro
145                 150                 155                 160

Gly Pro Cys Arg Gln Arg Val Val Met Glu Thr Ile Ala Val Gly Cys
                165                 170                 175

Thr Cys Ile

<210> SEQ ID NO 8
<211> LENGTH: 497
<212> TYPE: DNA
<213> ORGANISM: Homo sapiens

<400> SEQUENCE: 8
ggggttcctg gcgggtggca gctgcgggcc tgccgcctga cttggtggga tggactggcc      60
gcacagcctg ctcttcctcc tggccatctc catcttcctg gcgccaagcc accccggaa     120 caccaaaggc aaaagaaaag gcaagggag gcccagtccc ttggcccctg ggctcatcag     180
gtgccgctgg acctggtgtc tcgagtaaag ccctacgctc gaatggaaga gtatgagcgg     240
aaccttgggg agatggtggc ccagctgagg aacagctccg agccagccaa gaagaaatgt     300
gaagtcaatc tacagctgtg gttgtccaac aagaggagcc tgtccccatg gggctacagc     360
atcaaccacg accccagccg catccctgcg gacttgcccg aggcgcggtg cctatgtttg     420
ggttgcgtga atcccttcac catgcaggag gaccgtagca tggtgagcgt gccagtgttc     480
agccaggtgc cggtgcg                                                     497

<210> SEQ ID NO 9
<211> LENGTH: 160
<212> TYPE: PRT
<213> ORGANISM: Homo sapiens

<400> SEQUENCE: 9

Gln Pro Arg Ser Pro Lys Ser Lys Arg Lys Gly Gln Gly Arg Pro Gly
  1               5                  10                  15

Pro Leu Ala Pro Gly Pro His Gln Val Pro Leu Asp Leu Val Ser Arg
             20                  25                  30

Met Lys Pro Tyr Ala Arg Met Glu Glu Tyr Glu Arg Asn Ile Glu Glu
         35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

```
Trp Gly Tyr Ser Ile Asn His Asp Pro Ser Arg Ile Pro Val Asp Leu
                 85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Leu Cys Pro Pro Pro Arg Thr Gly Pro Cys Arg
        130                 135                 140

Gln Arg Ala Val Met Glu Thr Ile Ala Val Gly Cys Thr Cys Ile Phe
145                 150                 155                 160

<210> SEQ ID NO 10
<211> LENGTH: 160
<212> TYPE: PRT
<213> ORGANISM: Homo sapiens

<400> SEQUENCE: 10

Gln Pro Arg Ala Pro Lys Ser Arg Lys Gly Gln Gly Arg Pro Gly
1               5                   10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Leu Cys Pro Pro Pro Arg Thr Gly Pro Cys Arg
        130                 135                 140

Gln Arg Ala Val Met Glu Thr Ile Ala Val Gly Cys Thr Cys Ile Phe
145                 150                 155                 160

<210> SEQ ID NO 11
<211> LENGTH: 160
<212> TYPE: PRT
<213> ORGANISM: Homo sapiens

<400> SEQUENCE: 11

Gln Pro Arg Ser Pro Lys Ala Lys Arg Lys Gly Gln Gly Arg Pro Gly
1               5                   10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95
```

-continued

Pro Glu Ala Arg Cys Leu Cys Leu Gly Cys Val Asn Pro Phe Thr Met
              100                 105                 110

Gln Glu Asp Arg Ser Met Val Ser Val Pro Val Phe Ser Gln Val Pro
              115                 120                 125

Val Arg Arg Arg Leu Cys Pro Pro Pro Arg Thr Gly Pro Cys Arg
        130                 135                 140

Gln Arg Ala Val Met Glu Thr Ile Ala Val Gly Cys Thr Cys Ile Phe
145                 150                 155                 160

<210> SEQ ID NO 12
<211> LENGTH: 160
<212> TYPE: PRT
<213> ORGANISM: Homo sapiens

<400> SEQUENCE: 12

Gln Pro Arg Ser Pro Lys Ser Lys Arg Lys Gly Gln Gly Arg Pro Ala
1               5                   10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
    50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
        115                 120                 125

Val Arg Arg Arg Leu Cys Pro Pro Pro Arg Thr Gly Pro Cys Arg
    130                 135                 140

Gln Arg Ala Val Met Glu Thr Ile Ala Val Gly Cys Thr Cys Ile Phe
145                 150                 155                 160

<210> SEQ ID NO 13
<211> LENGTH: 160
<212> TYPE: PRT
<213> ORGANISM: Homo sapiens

<400> SEQUENCE: 13

Gln Pro Arg Ser Pro Lys Ser Lys Arg Lys Gly Gln Gly Arg Pro Gly
1               5                   10                  15

Pro Leu Ala Pro Gly Pro His Gln Val Pro Leu Asp Leu Val Ala Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
    50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

-continued

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
    130                 135                 140

Gln Arg Ala Val Met Glu Thr Ile Ala Val Gly Cys Thr Cys Ile Phe
145                 150                 155                 160

<210> SEQ ID NO 14
<211> LENGTH: 160
<212> TYPE: PRT
<213> ORGANISM: Homo sapiens

<400> SEQUENCE: 14

Gln Pro Arg Ser Pro Lys Ser Lys Arg Lys Gly Gln Gly Arg Pro Gly
1               5                   10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
    50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
    130                 135                 140

Gln Arg Val Val Met Glu Thr Ile Ala Val Gly Cys Thr Cys Ile Phe
145                 150                 155                 160

<210> SEQ ID NO 15
<211> LENGTH: 160
<212> TYPE: PRT
<213> ORGANISM: Homo sapiens

<400> SEQUENCE: 15

Gln Pro Arg Ser Pro Lys Ser Lys Arg Lys Gly Gln Gly Arg Pro Gly
1               5                   10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
    50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

-continued

Val Arg Arg Arg Leu Cys Pro Pro Pro Arg Thr Gly Pro Cys Arg
    130                 135                 140

Gln Arg Leu Val Met Glu Thr Ile Ala Val Gly Cys Thr Cys Ile Phe
145                 150                 155                 160

<210> SEQ ID NO 16
<211> LENGTH: 160
<212> TYPE: PRT
<213> ORGANISM: Homo sapiens

<400> SEQUENCE: 16

Gln Pro Arg Ser Pro Lys Ser Lys Arg Lys Gly Gln Gly Arg Pro Gly
1               5                   10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
        115                 120                 125

Val Arg Arg Arg Leu Cys Pro Pro Pro Arg Thr Gly Pro Cys Arg
    130                 135                 140

Gln Arg Phe Val Met Glu Thr Ile Ala Val Gly Cys Thr Cys Ile Phe
145                 150                 155                 160

<210> SEQ ID NO 17
<211> LENGTH: 160
<212> TYPE: PRT
<213> ORGANISM: Homo sapiens

<400> SEQUENCE: 17

Gln Pro Arg Ser Pro Lys Ser Lys Arg Lys Gly Gln Gly Arg Pro Gly
1               5                   10                  15

Pro Leu Ala Pro Gly Pro His Gln Val Pro Leu Asp Leu Val Gly Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
        115                 120                 125

Val Arg Arg Arg Leu Cys Pro Pro Pro Arg Thr Gly Pro Cys Arg
    130                 135                 140

```
Gln Arg Ala Val Met Glu Thr Ile Ala Val Gly Cys Thr Cys Ile Phe
145                 150                 155                 160
```

<210> SEQ ID NO 18
<211> LENGTH: 160
<212> TYPE: PRT
<213> ORGANISM: Homo sapiens

<400> SEQUENCE: 18

```
Gln Pro Arg Ser Pro Lys Ser Arg Lys Gly Gln Gly Arg Pro Ser
1               5                   10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
                100                 105                 110

Gln Glu Asp Arg Ser Met Val Ser Val Pro Val Phe Ser Gln Val Pro
                115                 120                 125

Val Arg Arg Arg Leu Cys Pro Pro Pro Arg Thr Gly Pro Cys Arg
                130                 135                 140

Gln Arg Ala Val Met Glu Thr Ile Ala Val Gly Cys Thr Cys Ile Phe
145                 150                 155                 160
```

<210> SEQ ID NO 19
<211> LENGTH: 160
<212> TYPE: PRT
<213> ORGANISM: Homo sapiens

<400> SEQUENCE: 19

```
Gln Pro Arg Ser Pro Lys Val Lys Arg Lys Gly Gln Gly Arg Pro Gly
1               5                   10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
                100                 105                 110

Gln Glu Asp Arg Ser Met Val Ser Val Pro Val Phe Ser Gln Val Pro
                115                 120                 125

Val Arg Arg Arg Leu Cys Pro Pro Pro Arg Thr Gly Pro Cys Arg
                130                 135                 140

Gln Arg Ala Val Met Glu Thr Ile Ala Val Gly Cys Thr Cys Ile Phe
145                 150                 155                 160
```

<210> SEQ ID NO 20
<211> LENGTH: 160
<212> TYPE: PRT
<213> ORGANISM: Homo sapiens

<400> SEQUENCE: 20

```
Gln Pro Arg Val Pro Lys Ser Lys Arg Lys Gly Gln Gly Arg Pro Gly
  1               5                  10                  15

Pro Leu Ala Pro Gly Pro His Gln Val Pro Leu Asp Leu Val Ser Arg
                 20                  25                  30

Met Lys Pro Tyr Ala Arg Met Glu Glu Tyr Glu Arg Asn Ile Glu Glu
             35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
                 85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
130                 135                 140

Gln Arg Ala Val Met Glu Thr Ile Ala Val Gly Cys Thr Cys Ile Phe
145                 150                 155                 160
```

<210> SEQ ID NO 21
<211> LENGTH: 158
<212> TYPE: PRT
<213> ORGANISM: Homo sapiens

<400> SEQUENCE: 21

```
Arg Ser Pro Lys Ser Lys Arg Lys Gly Gln Gly Arg Pro Gly Pro Leu
  1               5                  10                  15

Ala Pro Gly Pro His Gln Val Pro Leu Asp Leu Val Ser Arg Met Lys
                 20                  25                  30

Pro Tyr Ala Arg Met Glu Glu Tyr Glu Arg Asn Ile Glu Glu Met Val
             35                  40                  45

Ala Gln Leu Arg Asn Ser Ser Glu Leu Ala Gln Arg Lys Cys Glu Val
 50                  55                  60

Asn Leu Gln Leu Trp Met Ser Asn Lys Arg Ser Leu Ser Pro Trp Gly
 65                  70                  75                  80

Tyr Ser Ile Asn His Asp Pro Ser Arg Ile Pro Val Asp Leu Pro Glu
                 85                  90                  95

Ala Arg Cys Leu Cys Leu Gly Cys Val Asn Pro Phe Thr Met Gln Glu
            100                 105                 110

Asp Arg Ser Met Val Ser Val Pro Val Phe Ser Gln Val Pro Val Arg
            115                 120                 125

Arg Arg Leu Cys Pro Pro Pro Arg Thr Gly Pro Cys Arg Gln Arg
130                 135                 140

Ala Val Met Glu Thr Ile Ala Val Gly Cys Thr Cys Ile Phe
145                 150                 155
```

<210> SEQ ID NO 22
<211> LENGTH: 154

```
<212> TYPE: PRT
<213> ORGANISM: Homo sapiens

<400> SEQUENCE: 22

Ser Lys Arg Lys Gly Gln Gly Arg Pro Gly Pro Leu Ala Pro Gly Pro
 1               5                  10                  15

His Gln Val Pro Leu Asp Leu Val Ser Arg Met Lys Pro Tyr Ala Arg
             20                  25                  30

Met Glu Glu Tyr Glu Arg Asn Ile Glu Glu Met Val Ala Gln Leu Arg
         35                  40                  45

Asn Ser Ser Glu Leu Ala Gln Arg Lys Cys Glu Val Asn Leu Gln Leu
 50                  55                  60

Trp Met Ser Asn Lys Arg Ser Leu Ser Pro Trp Gly Tyr Ser Ile Asn
 65                  70                  75                  80

His Asp Pro Ser Arg Ile Pro Val Asp Leu Pro Glu Ala Arg Cys Leu
                 85                  90                  95

Cys Leu Gly Cys Val Asn Pro Phe Thr Met Gln Glu Asp Arg Ser Met
             100                 105                 110

Val Ser Val Pro Val Phe Ser Gln Val Pro Val Arg Arg Arg Leu Cys
             115                 120                 125

Pro Pro Pro Pro Arg Thr Gly Pro Cys Arg Gln Arg Ala Val Met Glu
         130                 135                 140

Thr Ile Ala Val Gly Cys Thr Cys Ile Phe
145                 150

<210> SEQ ID NO 23
<211> LENGTH: 151
<212> TYPE: PRT
<213> ORGANISM: Homo sapiens

<400> SEQUENCE: 23

Lys Gly Gln Gly Arg Pro Gly Pro Leu Ala Pro Gly Pro His Gln Val
 1               5                  10                  15

Pro Leu Asp Leu Val Ser Arg Met Lys Pro Tyr Ala Arg Met Glu Glu
             20                  25                  30

Tyr Glu Arg Asn Ile Glu Glu Met Val Ala Gln Leu Arg Asn Ser Ser
         35                  40                  45

Glu Leu Ala Gln Arg Lys Cys Glu Val Asn Leu Gln Leu Trp Met Ser
 50                  55                  60

Asn Lys Arg Ser Leu Ser Pro Trp Gly Tyr Ser Ile Asn His Asp Pro
 65                  70                  75                  80

Ser Arg Ile Pro Val Asp Leu Pro Glu Ala Arg Cys Leu Cys Leu Gly
                 85                  90                  95

Cys Val Asn Pro Phe Thr Met Gln Glu Asp Arg Ser Met Val Ser Val
             100                 105                 110

Pro Val Phe Ser Gln Val Pro Val Arg Arg Arg Leu Cys Pro Pro Pro
             115                 120                 125

Pro Arg Thr Gly Pro Cys Arg Gln Arg Ala Val Met Glu Thr Ile Ala
         130                 135                 140

Val Gly Cys Thr Cys Ile Phe
145                 150

<210> SEQ ID NO 24
<211> LENGTH: 160
<212> TYPE: PRT
<213> ORGANISM: Homo sapiens
```

```
<400> SEQUENCE: 24

His Pro Arg Asn Thr Lys Gly Lys Arg Lys Gly Gln Gly Arg Pro Ser
 1               5                  10                  15

Pro Leu Ala Pro Gly Pro His Gln Val Pro Leu Asp Leu Val Ser Arg
             20                  25                  30

Val Lys Pro Tyr Ala Arg Met Glu Glu Tyr Glu Arg Asn Leu Gly Glu
         35                  40                  45

Met Val Ala Gln Leu Arg Asn Ser Ser Glu Pro Ala Lys Lys Lys Cys
 50                  55                  60

Glu Val Asn Leu Gln Leu Trp Leu Ser Asn Lys Arg Ser Leu Ser Pro
 65                  70                  75                  80

Trp Gly Tyr Ser Ile Asn His Asp Pro Ser Arg Ile Pro Ala Asp Leu
                 85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
        115                 120                 125

Val Arg Arg Arg Leu Cys Pro Gln Pro Pro Arg Pro Gly Pro Cys Arg
    130                 135                 140

Gln Arg Val Val Met Glu Thr Ile Ala Val Gly Cys Thr Cys Ile Phe
145                 150                 155                 160

<210> SEQ ID NO 25
<211> LENGTH: 158
<212> TYPE: PRT
<213> ORGANISM: Homo sapiens

<400> SEQUENCE: 25

Arg Asn Thr Lys Gly Lys Arg Lys Gly Gln Gly Arg Pro Ser Pro Leu
 1               5                  10                  15

Ala Pro Gly Pro His Gln Val Pro Leu Asp Leu Val Ser Arg Val Lys
             20                  25                  30

Pro Tyr Ala Arg Met Glu Glu Tyr Glu Arg Asn Leu Gly Glu Met Val
         35                  40                  45

Ala Gln Leu Arg Asn Ser Ser Glu Pro Ala Lys Lys Lys Cys Glu Val
 50                  55                  60

Asn Leu Gln Leu Trp Leu Ser Asn Lys Arg Ser Leu Ser Pro Trp Gly
 65                  70                  75                  80

Tyr Ser Ile Asn His Asp Pro Ser Arg Ile Pro Ala Asp Leu Pro Glu
                 85                  90                  95

Ala Arg Cys Leu Cys Leu Gly Cys Val Asn Pro Phe Thr Met Gln Glu
            100                 105                 110

Asp Arg Ser Met Val Ser Val Pro Val Phe Ser Gln Val Pro Val Arg
        115                 120                 125

Arg Arg Leu Cys Pro Gln Pro Pro Arg Pro Gly Pro Cys Arg Gln Arg
    130                 135                 140

Val Val Met Glu Thr Ile Ala Val Gly Cys Thr Cys Ile Phe
145                 150                 155

<210> SEQ ID NO 26
<211> LENGTH: 153
<212> TYPE: PRT
<213> ORGANISM: Homo sapiens

<400> SEQUENCE: 26

Lys Arg Lys Gly Gln Gly Arg Pro Gly Pro Leu Ala Pro Gly Pro His
```

-continued

```
                1               5                      10                         15
Gln Val Pro Leu Asp Leu Val Ser Arg Met Lys Pro Tyr Ala Arg Met
                        20                      25                      30

Glu Glu Tyr Glu Arg Asn Ile Glu Glu Met Val Ala Gln Leu Arg Asn
                35                      40                      45

Ser Ser Glu Leu Ala Gln Arg Lys Cys Glu Val Asn Leu Gln Leu Trp
        50                      55                      60

Met Ser Asn Lys Arg Ser Leu Ser Pro Trp Gly Tyr Ser Ile Asn His
65                      70                      75                      80

Asp Pro Ser Arg Ile Pro Val Asp Leu Pro Glu Ala Arg Cys Leu Cys
                        85                      90                      95

Leu Gly Cys Val Asn Pro Phe Thr Met Gln Glu Asp Arg Ser Met Val
                100                     105                     110

Ser Val Pro Val Phe Ser Gln Val Pro Val Arg Arg Leu Cys Pro
                        115                     120                     125

Pro Pro Pro Arg Thr Gly Pro Cys Arg Gln Arg Ala Val Met Glu Thr
        130                     135                     140

Ile Ala Val Gly Cys Thr Cys Ile Phe
145                     150
```

<210> SEQ ID NO 27
<211> LENGTH: 128
<212> TYPE: PRT
<213> ORGANISM: Homo sapiens

<400> SEQUENCE: 27

```
Met Lys Pro Tyr Ala Arg Met Glu Glu Tyr Glu Arg Asn Ile Glu Glu
1               5                      10                      15

Met Val Ala Gln Leu Arg Asn Ser Ser Glu Leu Ala Gln Arg Lys Cys
                20                      25                      30

Glu Val Asn Leu Gln Leu Trp Met Ser Asn Lys Arg Ser Leu Ser Pro
                35                      40                      45

Trp Gly Tyr Ser Ile Asn His Asp Pro Ser Arg Ile Pro Val Asp Leu
        50                      55                      60

Pro Glu Ala Arg Cys Leu Cys Leu Gly Cys Val Asn Pro Phe Thr Met
65                      70                      75                      80

Gln Glu Asp Arg Ser Met Val Ser Val Pro Val Phe Ser Gln Val Pro
                        85                      90                      95

Val Arg Arg Leu Cys Pro Pro Pro Arg Thr Gly Pro Cys Arg
                100                     105                     110

Gln Arg Ala Val Met Glu Thr Ile Ala Val Gly Cys Thr Cys Ile Phe
                115                     120                     125
```

<210> SEQ ID NO 28
<211> LENGTH: 157
<212> TYPE: PRT
<213> ORGANISM: Homo sapiens

<400> SEQUENCE: 28

```
Arg Ser Pro Lys Ser Lys Arg Lys Gly Gln Gly Arg Pro Gly Pro Leu
1               5                      10                      15

Ala Pro Gly Pro His Gln Val Pro Leu Asp Leu Val Ser Arg Met Lys
                20                      25                      30

Pro Tyr Ala Arg Met Glu Glu Tyr Glu Arg Asn Ile Glu Glu Met Val
        35                      40                      45

Ala Gln Leu Arg Asn Ser Ser Glu Leu Ala Gln Arg Lys Cys Glu Val
```

-continued

```
                50                      55                     60
Asn Leu Gln Leu Trp Met Ser Asn Lys Arg Ser Leu Ser Pro Trp Gly
65                  70                  75                  80

Tyr Ser Ile Asn His Asp Pro Ser Arg Ile Pro Val Asp Leu Pro Glu
            85                  90                  95

Ala Arg Cys Leu Cys Leu Gly Cys Val Asn Pro Phe Thr Met Gln Glu
            100                 105                 110

Asp Arg Ser Met Val Ser Val Pro Val Phe Ser Gln Val Pro Val Arg
            115                 120                 125

Arg Arg Leu Cys Pro Pro Pro Arg Thr Gly Pro Cys Arg Gln Arg
    130                 135                 140

Ala Val Met Glu Thr Ile Ala Val Gly Cys Thr Cys Ile
145                 150                 155
```

METHODS FOR PROMOTING PRODUCTION OF MYELIN BY SCHWANN CELLS

This claims the benefit of U.S. Provisional Patent Application No. 60/185,666 filed on Feb. 29, 2000.

BACKGROUND OF THE INVENTION

The peripheral nervous system (PNS) serves as a bridge between the environment and the central nervous system (CNS). The PNS is comprised of primary afferent neurons, which sends information from sensory receptors to the CNS, somatic motor neurons, which transmit electrical stimuli from the CNS to voluntary muscles, and autonomic motor neurons, which transmit electrical stimuli to cardiac muscle, smooth muscle or glands. A neuron generally has a cell body, and an axon, which is a long nerve cell process extending from the cell body that is capable of rapidly conducting nerve impulses over long distances so as to deliver signals to cells. The axons of many vertebrate neurons are insulated by a myelin sheath, which greatly increases the rate at which an axon can conduct an action potential. Schwann cells are responsible for myelinating nerve cells in the peripheral nervous system. The Schwann cells wrap layer upon layer of their own plasma membrane in a tight spiral around the axon thereby insulating the axonal membrane so that almost no current leaks across it. Unmyelinated axons in the PNS are nonetheless embedded in Schwann cells although they are not ensheathed by myelin.

A number of neuropathies of the PNS are associated with demyelination or failure of the Schwann cells to properly ensheath the axons of the PNS. They are diabetic neuropathy, Guillain-Barré disease (acute demyelinating polyneuropathy), chronic inflammatory demyelinating polyradiculoneuropathy (CIPD), and HIV inflammatory demyelinating disease. Also axon damage due to physical trauma may result in demyelination of the PNS. Thus, there is a need to discover agents that can be used to promote the production of myelin by Schwann cells.

DESCRIPTION OF THE INVENTION

The present invention fills this need by providing for a method for promoting production of myelin or P zero protein by Schwann cell comprising bringing a Zcyto7 polypeptide or IL-17 into contact with Schwann cells. Examples of Zcyto7 polypeptides are the polypeptides of SEQ ID NOs: 2, 7, and 9–28.

Preferably, the mammal treated will be a human and the Zcyto7 will be of the human allotypes. Preferably, the Zcyto7 will be administered in an amount of about 0.1 to 100 micrograms (µg) per kilogram of body weight.

The teachings of all of the references cited in the present specification are incorporated in their entirety herein by reference.

Definitions

The term "effective amount" as used herein regarding the effective amount of Zcyto7 administered in accordance with the present invention means an amount of Zcyto7 that causes increased expression of myelin by Schwann cells. The effective amount of Zcyto7 or IL-17 to be administered is from 0.1 µg to 1 mg of Zcyto7 or IL-17 per kilogram of body weight per day. More preferably, the effective amount is from 1 µg to 500 µg of Zcyto7 or IL-17 per kilogram of body weight. Zcyto7 should be administered daily until the symptoms of neuropathy dissipate.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

Zcyto7 and a method for making Zcyto7 polypeptides have been disclosed in International Patent Application No. PCT/US98/08212, Publication No. WO 98/49310.

Introduction

The present invention is based upon the discovery that Zcyto7 or IL-17 can induce the production of myelin by Schwann cells. The present invention is also based upon the discovery that Zcyto7 can induce the production of protein zero by Schwann Cells. Protein zero is a major structural protein of peripheral myelin, and is a homophilic immunoglobulin cell adhesion molecule, which mediates adhesion of Schwann cell membranes as they enwrap axons and generate compact myelin, Spiryda L. B., *J. Neurosci, Res.* 54: 137–146 (1998).

The axons of many vertebrate neurons are insulated by a myelin sheath, which greatly increases the rate at which an axon can conduct an action potential. Schwann cells, which are supporting or glial cells, form myelin in the peripheral nerves. The Schwann cells wrap layer upon layer of their own plasma membrane in a tight spiral around the axon, thereby insulating the axonal membrane so that almost no current leaks across it. The sheath is interrupted at regularly spaced intervals called the 'nodes of Ranvier', where almost all the $Na^+$ channels in the axon are concentrated. Because the ensheathed portions of the axon membrane are so well insulated, a depolarization of the membrane at one node almost immediately spreads passively to the next node. Thus, an action potential propagates along a myelinated axon by jumping from node to node, a process called salutatory conduction. This type of conduction has two main advantages: action potentials travel faster, and metabolic energy is conserved because the active excitation is confined to the small regions of axonal plasma membrane at nodes of Ranvier. Conduction in myelinated axons is characterized by a rapid electronic conduction (because of the decreased time constant for conduction) with little decrement (because of the increased length constant) between the nodes of Ranvier. Only at the nodes is the action potential regenerated. A myelination of an axon increases electronic conduction velocity by sevenfold.

Myelinated axons are also more efficient metabolically than nonmyelinated axons. The sodium-potassium pump extrudes the sodium that enters and re-accumulates the potassium that leaves the cell during action potentials. In a myelinated axon, ionic currents are restricted to the small fraction of the membrane surface at the nodes of Ranvier. For this reason fewer $Na^+$ and $K^+$ ions traverse a unit area of membrane, and less ion pumping is required to maintain $Na^+$ and $K^+$ gradients.

The present invention is a method for inducing the expression of myelin or Protein zero by Schwann cells. Thus, Zcyto7 can be administered to treat a number of demyelinating PNS neuropathies, or to induce the production of myelin around regenerating peripheral nerve cells that have been injured by trauma.

Those skilled in the art will recognize that the sequences disclosed in SEQ ID NOS: 1, and 2 represent a single allele of the human Zcyto7. One can clone allelic variants of these sequences by probing cDNA or genomic libraries from different individuals according to standard procedures.

Acute Demyelinating Polyneuropathy

An example of a demyelinating disease of the PNS is acute demyelinating polyneuropathy. This acute inflammatory polyneuropathy, also known as Guillain-Barré syndrome (GBS), occurs in all parts of the world and in all seasons. It affects children and adults of all ages and both sexes. A mild respiratory or gastrointestinal infection precedes the neuritic symptoms by 1 to 3 weeks in about 60 percent of the patients. Other less common antecedent events include surgical procedures, viral exanthems and other viral illnesses such as cytomegalovirus, Epstein-Barr virus, human immunodeficiency virus (HIV), bacterial infections, e.g., *Mycoplasma pneumoniae*, Lyme disease and particularly *Campylobacter jejuni*, and lymphoma, particularly Hodgkin's disease.

Symptomatology

The major clinical manifestation of GBS is weakness, which evolves, more or less symmetrically, over a period of several days or a week or two. Proximal as well as distal muscles of the limbs are involved, usually the lower extremities before the upper trunk, intercostals, neck, and cranial muscles are affected later. The weakness can progress to total motor paralysis with death from respiratory failure within a few days. More than half of the patients complain of pain and an aching discomfort in the muscles, mainly those of the hips, thighs, and back. Paresthesias (tingling, burning, numbness) are also a frequent and early symptom but tend to be evanescent; occasionally they are absent throughout the illness. The most important laboratory aids are the cerebrospinal fluid (CSF) examination and electrodiagnostic studies. An increase in CSF protein is probably due to widespread inflammatory disease of the nerve roots. In a few patients (10 percent or less), the CSF protein values are normal throughout the illness.

Electrodiagnostic studies may be normal early in the illness. Then there occurs a reduction in conduction velocity or conduction block in motor neurons. Prolonged distal latencies and abnormal F responses (with affection of proximal parts of nerves) are other diagnostic findings.

Treatment

Most of the evidence suggests that the clinical manifestations of this disorder are the result of a cell-mediated immunologic reaction directed at peripheral nerves. In general administration of Zcyto7 should begin upon diagnosis of the disease at the dosages listed below. However, treatment with Zcyto7 may be delayed until the underlying inflammatory condition has subsided. Plasma exchange or intravenous administration of immunoglobulin can be employed to alleviate the inflammatory condition. For best results this should be done within two weeks of onset of symptoms. The usual plasma exchange regimen removes 200 to 250 mL/kg in four to six treatments on alternate days. The usual replacement fluid is saline and 5 percent albumin. Alternatively immunoglobulin can be administered at 0.4 g/kg/day for 5 consecutive days. Zcyto7 can be administered at the onset of the disease, during treatment to alleviate the inflammatory process or after the treatment. Administration of Zcyto7 should be continued on a regular basis, at least 1–3 times a week until full neurologic recovery by the patient.

In chronic inflammatory demyelinating polyradiculoneuropathy, other immunosuppressants and plasmapheresis can be used to alleviate the inflammatory condition and Zcyto7 can be administered to promote remyelination.

Diabetic Neuropathies

Zcyto7 can also be used to promote myelination expression in Schwann cells to treat diabetic neuropathies. The demyelination that occurs in diabetes mellitus is believed to be caused by ischemia. The patient should be administered Zcyto7 1 to 3 times a week at the dosages listed below.

Use of Zcyto7 to Promote Re-myelination of Peripheral Neurons Injured by Trauma

Unlike the central nervous system the neurons of the PNS have the ability to regenerate or repair themselves after injury caused by trauma. After an axon of the PNS is lost through trauma, the proximal stump of the damaged axon develops sprouts. In the PNS these sprouts elongate and grow along the path of the original nerve if this route is available. The Schwann cells in the distal stumps of the nerve not only survive the degeneration of the neuron, but they also proliferate and form rows along the course previously taken by the axons. Growth cones of the sprouting axons find their way along the rows of Schwann cells and may eventually reinnervate the original peripheral target structures. The Schwann cells then remyelinate the axons. To expedite the generation of the myelin sheath around the newly formed axon, Zcyto7 can be administered, preferably every one to three days until it becomes apparent the nerve is regenerated by means of the appropriate neurological test.

Modes of Administration

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a Zcyto7 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., (Mack Publishing Co., Easton, Pa., 19th ed., 1995). Therapeutic doses will generally be in the range of 0.1 to 100 µg/kg of patient weight per day, preferably 0.5–20 µg/kg per day, with the exact dose determined by the clinician according to accepted standards determination of dose is within the level of ordinary skill in the art. The proteins may be administered for acute treatment, over one week or less, often over a period of one to three days or may be used in chronic treatment, over several months or years.

Nucleic Acid-based Therapeutic Treatment

Zcyto7 can be also administered by means of gene therapy. In one embodiment, a gene encoding a Zcyto7 polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector [Kaplitt et al., *Molec. Cell. Neurosci*.2: 320–330 (1991)], an attenuated adenovirus vector, such as the vector described by Stratford-Perricaudet et al., *J. Clin. Invest.* 90:626–630 (1992), and a defective adeno-associated virus vector [Samulski et al., *J. Virol.,* 61:3096–3101 (1987); Samulski et al. *J. Virol.,* 63:3822–3828 (1989)].

In another embodiment, the gene can be introduced in a retroviral vector, e.g., as described in Anderson et al., U.S. Pat. No. 5,399,346; Mann et al., *Cell,* 33:153 (1983); Temin et al., U.S. Pat. No. 4,650,764; Temin et al., U.S. Pat. No. 4,980,289; Markowitz et al., *J. Virol.* 62:1120 (1988); Temin et al., U.S. Pat. No. 5,124,263; International Patent Publication No. WO 95/07358, published Mar. 16, 1995 by Dougherty et al. and *Blood,* 82:845 (1993).

Alternatively, the vector can be introduced by lipofection in vivo using liposomes. Synthetic cationic lipids can be used to prepare liposomes for in vivo transfection of a gene encoding a marker [Felgner et al., *Proc. Natl. Acad. Sci. USA,* 84:7413–7417 (1987); see Mackey et al., *Proc. Natl. Acad. Sci. USA,* 85:8027–8031 (1988)]. The use of lipofection to introduce exogenous genes into specific organs in vivo has certain practical advantages. Molecular targeting of liposomes to specific cells represents one area of benefit. It is clear that directing transfection to particular cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting. Targeted peptides, e.g., hormones or neurotransmitters, and proteins such as antibodies, or non-peptide molecules could be coupled to liposomes chemically.

It is possible to remove the cells from the body and introduce the vector as a naked DNA plasmid and then re-implant the transformed cells into the body. Naked DNA vector for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter [see, e.g., Wu et al., *J. Biol. Chem.,* 267:963–967 (1992); Wu et al., *J. Biol. Chem.,* 263:14621–14624 (1988)].

EXAMPLE 1

Cloning of Zcyto7

Zcyto7 was identified from expressed sequence tag (EST) 582069 (SEQ ID NO: 3) by its homology to Interleukin-17. The EST582069 cDNA clone was obtained from the IMAGE™ consortium Lawrence Livermore National Laboratory through Genome Systems, Inc. The cDNA was supplied as an agar stab containing *E. coli* transfected with the plasmid having the cDNA of interest and then streaked out on an LB 100 μg/ml ampicillin and 100 μg/ml methicillin plate. The cDNA insert in EST582069 was sequenced. The insert was determined to be 717 base pairs long with a 180 amino acid open reading frame and a 22 amino acid signal peptide.

EXAMPLE 2

Construction of Zcyto7 Expression Vectors

A 473 bp Zcyto7 PCR DNA fragment was generated with 1 μl of a dilution of the EST582069 plasmid prep of Example 2 and 20 picomoles (pm) of primer SEQ ID NO: 4 and 20 pm primer SEQ ID NO: 5. The digested reaction mixture was electrophoresed on a 1% TBE gel; the DNA band was excised with a razor blade and the DNA was extracted from the gel with the Qiaquick<<Gel Extraction Kit (Qiagen). The excised DNA was subcloned into plasmid nfpzp9, which had been cut with Bam and Xho. Nfpzp9 is a mammalian cell expression vector comprising an expression cassette containing the mouse metallothionein-1 promoter, a sequence encoding the tissue plasminogen activator (TPA) leader, then multiple restriction sites. These were followed by the human growth hormone terminator, an *E. coli* origin of replication and a mammalian selectable marker expression unit containing the SV40 promoter, enhancer and origin of replication, a dihydrofolate reductase gene (DHFR) and the SV40 terminator.

Zcyto7 was purified by means of affinity chromatography using anti-Zcyto7 antibodies.

EXAMPLE 3

Cloning of Murine Zcyto7

Mouse Zcyto7 was identified from an expressed sequence tag (EST) 660242 (SEQ ID NO: 8) by its homology to human Zcyto7. EST660242 cDNA clone was obtained from the IMAGE consortium Lawrence Livermore National Laboratory through Genome Systems, Inc. The cDNA was supplied as an agar stab containing *E. coli* transfected with the plasmid having the cDNA of interest and then streaked out on an LB 100 μg/ml ampicillin, 25 μg/ml methicillin plate. The cDNA insert in EST660242 was sequenced. The insert was determined to be 785 base pairs with an open reading frame of 180 amino acids and a putative 20 amino acid signal peptide. The sequences are defined by SEQ ID NO: 7 and SEQ ID NO: 6.

EXAMPLE 4

Induction of Myelin Expression by Zcyto7

OBJECT

The object of the present experiment was to determine if Zcyto7 could induce the expression of myelin by Schwann cells.

TEST SYSTEM

Primary Schwann cell cultures and dorsal root ganglia (DRG)-Schwann cell co-cultures were established. Rat primary Schwann cells were isolated as described by Einheber et al., *J. Cell Biol.* 123:1223–1236 (1994). Schwann cells were grown in 100 mm poly-L-lysine coated plates in Dulbecco's modified Eagles medium (DMEM) supplemented with 10% fetal bovine serum (FBS), pituitary extract (1 mg/ml) and 10 μM forskolin; up to 80–90% confluency.

Dissociated neuronal cultures from normal rats were established as described by Kleitman et al., Tissue culture methods for the study of myelination, in *Culturing Nerve Cells,* Banker and Goslin, Eds, pp. 338–378(MIT Press, Cambridge, Mass., 1992). Briefly, DRG were dissected out from the rats, treated with 0.25% trypsin, mechanically dissociated, washed, and resuspended in L15 medium with 10% fetal calf serum. The neurons were plated onto 12-mm glass coverslips coated with ammoniated rat tail collagen (Biomedical Technologies, Inc.) for microscopic evaluation. Starting one day following the dissection, cultures were treated over a 2-week period with three cycles of 5-fluorodeoxyuridine and uridine (both at 10 μM) in standard medium to assure a pure neuronal population. Standard medium consisted of minimum essential medium (MEM) supplemented with 10% FBS, 2 mM glutamine, 0.4% glucose, and 50 ng/m β-nerve growth factor (β-NGB).

Myelinating co-cultures were established by seeding the purified neurons with rat primary Schwann cells as described Einheber, et al., id.

TEST ARTICLE AND FORMULATION METHODS

Four solutions of Zcyto7, A258F, A258G, A275F and A311F, were analyzed all of which had been expressed in Baby Hamster Kidney (BHK) cells. Solution A258F contained human Zcyto7 at a concentration of 0.603 mg/ml of phosphate buffered saline (PBS) at pH 6.0. Solution A258G contained human Zcyto7 at a concentration of 0.089 mg/ml of PBS+0.1% BSA at a pH of 6.0. Solution A311 contained human Zcyto7 that had been dimerized by fusing an Immunoglobulin (Ig) Fc portion to the carboxy terminus of the polypeptide; the concentration of the Zcyto7 fusion protein was at 0.45 mg/ml of PBS at pH 7.0. Solution A275F contained murine Zcyto7 at a concentration of 1 mg/ml of PBS at pH 6.0. A control of PBS was also tested. Also tested was a solution of IL-17 at a concentration of 50 µg/ml of PBS, pH 7.0.

A solution of progesterone (Sigma) at a concentration of 1 mg/ml of ethanol was also prepared.

METHODS

EXPERIMENT 1

EFFECT OF ZCYTO7 IN PURE SCHWANN CELLS

The effect of Zcyto7 was tested in pure Schwann cell culture and in a co-culture of DRG and Schwann cells. Primary Schwann cells were grown to 80–90% confluency in 100 mm plates as described above. 12 h before treatment media was changed to 10 ml of N2 (defined medium) with or without 1 µM progesterone. The Zcyto7 solutions were added as 1.1 ml of 10×solution in N2 media, and cells were incubated for 48 hours (h). Cells were washed once with Hanks balanced salt solution (HBSS). The cell suspension was frozen on dry ice, thawed, pelleted and resuspended in 100 µl of lysis buffer, 125 mM tris (hydroxymethyl) aminomethane HCl (Tris HCl) pH7.0, 15% sucrose, 4% sodium dodecyl sulfate (SDS), 10 mM ethylenediaminetetraacetic acid (EDTA). Lysates were boiled for 5 minutes (min) on a water bath and cooled on ice. The protein concentration was determined using 4 µl in a BioRad BCA assay. Each sample was then supplemented with dithiothreitol (DTT) to a final concentration of 10 mM phenylmethylsulfonyl fluoride (PMSF)—to 2 mM, pepstatin and leupeptin—to 10 µg/ml.

60 µg of protein from each sample were separated on 4–12% Tris-Glycin NOVEX gels at 125 V constant for 1.5 h. Each gel contained vehicle control, vehicle supplemented with progesterone control, and randomly chosen samples from treatment groups. Transfer to poly (vinylidine difluoride) (PVFD) membrane was carried out according to the NOVEX electrotransfer protocol, at 25 V, for 40 min. Membranes were rinsed with tris buffered saline (TBS) for 3 min, and blocked with TBS/0.1% TWEEN-20/2% BSA for 1 h. Membranes were then incubated with 1:1000 dilution of anti-MBP mouse monoclonal IgG (Boehringer, Mannheim) in TBS/0.1% TWEEN-20, 0.5% BSA overnight, at 4° C. After washing 4 times for 30 min with TBS/0.1% TWEEN-20, membranes were incubated with anti-mouse horseradish peroxidase conjugate (1:20,000 dilution in TBS/0.1% TWEEN-20, incubated with SUPERSIGNAL chemiluminescent HRP substrate (Pierce Chemical Co., Rockford, Ill.) and exposed to Kodak X-Ray film for 15–20 min.

Density of myelin basic protein (MBP) bands was measured on LYNX Densitometer (Applied imaging) with ILLUMA System and expressed as percent progesterone-induced control MBP.

EXPERIMENT 2

PRODUCTION OF MYELIN IN DRG-SCHWANN CELL (DRG-SC) CO-CULTURES

After establishing the myelinating co-cultures, Schwann cells were allowed to proliferate for one week attached to the neurons. The medium was then changed to 15% and 50 µg/ml ascorbate was added to promote basal lamina formation and to initiate myelination. The effect of the Zcyto7 was evaluated for 3.5 weeks in the presence of ascorbate, with the medium changed every two days. Cultures were then fixed in 3.7% formaldehyde for 10 minutes and made permeable in 100% methanol for 15 minutes at −20° C. Following with PBS having 3% BSA, the samples were incubated with mouse anti-MBP antibody (Boehringer-Mannheim) overnight, washed and incubated with Cy3-labeled anti-mouse IgG. Samples were washed, mounted in VECTASHIELD and examined by epifluorescence with a Zeiss AXIOSKOP microscope.

Myelin production was quantitatively and qualitatively evaluated, and myelin density was determined for each of the five replicates per condition. Six representative regions in each sample were captured using a low-level light COHUE digital camera, and the density of fluorescent signal determined using the National Institutes of Health (NIH) Scion Image. The mean and standard deviation of myelin density was calculated for each group and converted to a percentage by dividing by the density seen in the appropriate control culture. Morphometric measurements were carried out using double blind analysis.

EXPERIMENTAL DESIGN

In experiment 1, the effect of the 4 different solutions of Zcyto7 on MBP accumulation was evaluated in pure Schwann cell cultures, with and without progesterone pre-treatment. Solution A275F was evaluated in experiment 1 at 1 ng/ml, 10 ng/ml, 100 ng/ml and 1 µg/ml.

Four controls were included in each experiment: test vehicle alone, vehicle supplemented with progesterone, vehicle supplemented with IL-17, and vehicle supplemented with progesterone and IL-17 [See *J. Immunol*, 150:5445–5456 (1993)]. Three replicates were set up per each condition.

Solution A258F was chosen on the basis of the results of experiment 1 was evaluated in experiment 2 for myelin formation in DRG-Schwann co-cultures.

Concentrations of A258F of 1 ng/ml, 10 ng/ml, and 100 ng/ml were tested without the addition of progesterone, and a sample having a concentration of 100 ng/ml with the addition of progesterone was tested. Five controls were included: test vehicle alone, vehicle supplemented with ascorbate, vehicle supplemented with ascorbate plus progesterone and vehicle supplemented with ascorbate plus IL17, at 10 ng/ml and 100 ng/ml.

RESULTS

Table 1 shows the mean induction±standard deviation (SD) for each solution of Zcyto7. Treatment of pure Schwann cell cultures with Zcyto7 no matter from which solution resulted in various degrees of MBP induction. The best results were obtained with solution A258F. It induced MBP accumulation in dose-dependent manner, with maximal effect at 100 ng/ml. In contrast to the other compounds, culture-to-culture variability was minimal.

Pretreatment of the Schwann cell cultures with progesterone appears to mediate the induction of MBP in all cases. However, even in the absence of progesterone pretreatment, solutions A258F, A258G and A275F significantly induced MBP accumulation at 100 ng/ml.

TABLE 1

Mean MBP induction after treatment with Zcyto7 (as percent of progesterone induction)

| TREATMENT | A275 F | A311 F | A258 F | A258 G |
|---|---|---|---|---|
| Media | 53.1 ± 15.49 | 56.49 ± 7.85 | 36.87 ± 34.92 | 6.667 ± 2.667 |
| Prog + 1 ng/ml | 48.77 ± 45.44 | 187.20 ± 90.33 | 117.00 ± 15.83 | |
| Prog + 10 ng/ml | 121.00 ± 78.16 | 208.80 ± 87.13 | 187.20 ± 18.43 | |
| Prog + 100 ng/ml | 278.00 ± 95.43 | 296.20 ± 190.30 | 265.90 ± 32.09 | 152 ± 19.38 |
| Prog + 1 µg/ml | 280.80 ± 62.95 | 302.40 ± 222.20 | 174.30 ± 25.59 | |
| Prog + IL-17 | 214.50 ± 103.80 | 180.60 ± 123.80 | 199.30 ± 23.21 | |
| 1 ng/ml | 102.40 ± 21.33 | 150.50 ± 86.65 | 81.47 ± 7.75 | |
| 10 ng/ml | 123.40 ± 50.34 | 120.10 ± 157.30 | 41.59 ± 32.29 | |
| 100 ng/ml | 210.60 ± 9708 | 223.30 ± 39.27 | 117.00 ± 42.89 | 210 ± 115.20 |
| 1 µg/ml | 170.90 ± 49.63 | 210.20 ± 73.93 | 152.80 ± 27.95 | |

TABLE 2

MBP signal density in various DRG-Schwann cell co-culture treatment groups

| Treatment | MBP Signal Density (mean ± SD) |
|---|---|
| Ascorbic acid (AA) + vehicle | 13.31 ± 1.92 |
| AA + IL-17 10 ng/ml | 11.65 ± 0.78 |
| AA + IL-17 100 ng/ml | 100 ng/ml |
| AA + A258F 1 ng/ml | 20.04 ± 8.55 |
| AA + A258F 10 ng/ml | 47.74 ± 23.60 |
| AA + A258F 100 ng/ml | 74.74 ± 19.22 |
| Vehicle | 3.949 ± 1.88 |

TABLE 3

Mean MBP induction after treatment with IL-17 (as percent of progesterone induction)

| IL-17 | 398.40 ± 104.90 | 290.40 ± 51.42 | 423.50 ± 31.34 |
|---|---|---|---|

EXAMPLE 5

Induction of the Expression of Protein Zero by Zcyto7

The present example shows that Zcyto7 induces Schwann cells to produce Protein Zero.

Material and Methods

Primary Schwann cells were prepared as described above using 1-day old CD rat neonates. Schwann cells were grown in DMEM, 10% fetal bovine serum (FBS), plus bovine pituitary extract (PEX) at 20 µg/ml and Forskolin at 2µM. The cells were weaned down to a low serum medium ("Li" medium with 1% FBS added to it). Li medium was comprised of DMEM/F12, 10 µg/ml tranferrin, 5 µg/ml insulin, 2 nM progesterone, 2 µM Forskolin, 20 µg/ml PEX, and 20 ng/ml Heregulin-beta-1 (R & D Systems).

The Schwann cells were grown to confluency in the low serum growth medium on poly-L-lysine-coated 10 cm tissue culture dishes. The cell medium was changed to N2 medium+1 µM progesterone with either Forskolin (Calbiochem) (10 µM and 25 µM) or 100 ng/ml of human Zcyto7. Control medium was Schwann cells in N2+1 µM progesterone for the whole time. Cells were harvested and placed in lysis buffer (125 mM Tris HCl, pH 7.0, 15% sucrose, 4% SDS, 10 mM EDTA, plus added Roche Complete-EDTA-free, protease inhibitor cocktail).

Western Blot Analysis:

Protein concentrations of cell lysates were determined by Pierce BCA protein assay (Pierce Chemical Co., Rockford, Ill.). Forty micrograms of each cell lysate sample was run on a 4–12% Tris-Glycine gel (Novex) at 125 V for 1 hour 30 minutes, and transferred onto a PVDF membrane in a Hoeffer unit a 550 mAmps for 1 hour. Mouse monoclonal antibody to protein zero was used at 1:1000 dilution (1 µg/am final concentration) to probe the blot. A Vectastain biotin/streptavidin-HRP $2^{nd}$ antibody system was used for amplication. The blot was developed with Pierce SuperSignal West Pico chemiluminescent substrate and scanned on a Boehringer-Mannheim Lumi-Imager.

Results:

The results indicate that 100 ng/ml of human Zcyto7 induces the expression of protein zero by primary rat Schwann cells. Values calculated by the LumiAnalyst program showed induction of protein zero by Zcyto7 to be increased over the control cell culture medium. Designating the amount of P zero protein in the band for the media control as 100%, the relative percentage for human Zcyto7-treated Schwann cells was 173%. The positive control of Forskolin also showed an induction of P zero protein having a relative percentage of P zero protein of 199% at 10 µM, and 30% at 25 µM relative to the cell culture control medium.

EXAMPLE 6

Hybridization Studies

The expression of myelin basic protein and protein zero was also determined by measuring the mRNA levels that encode myelin basic protein and protein zero. The results showed that the mRNA that encodes for myelin basic protein and the mRNA that encodes for protein zero were upregulated by Zcyto7.

We claim:

1. A method for promoting the production of myelin by Schwann cells in an individual suffering from acute demyelinating polyneuropathy, diabetic neuropathies, or trauma-induced peripheral nerve injury comprising administering to said individual a pharmaceutically effective amount of a polypeptide comprised of the amino acid sequence of SEQ ID NO: 9.

* * * * *